United States Patent [19]

Weisert et al.

[11] Patent Number: 4,816,044
[45] Date of Patent: Mar. 28, 1989

[54] APPARATUS FOR THE DEGASIFICATION OF FLUSHING WATER

[75] Inventors: Willi Weisert, Oberderdingen; Hugo Wetzel, Gondelsheim, both of Fed. Rep. of Germany

[73] Assignee: Riwoplan Medizin-Technische Einrichtungsgesellschaft, Fed. Rep. of Germany

[21] Appl. No.: 165,010

[22] Filed: Mar. 7, 1988

[30] Foreign Application Priority Data

Mar. 5, 1987 [DE] Fed. Rep. of Germany ....... 3707071

[51] Int. Cl.⁴ ............................................. B01D 19/00
[52] U.S. Cl. ........................................ 55/164; 55/194; 55/195
[58] Field of Search ............................. 55/52, 164–170, 55/190, 191, 194, 195

[56] References Cited

U.S. PATENT DOCUMENTS

| | | | |
|---|---|---|---|
| 1,401,116 | 12/1921 | Ehrhart | 55/195 X |
| 1,618,424 | 2/1927 | Gibson | 55/195 X |
| 1,776,019 | 9/1930 | Elliott | 55/165 |
| 1,836,338 | 12/1931 | Rodman et al. | 55/194 X |
| 1,910,088 | 5/1933 | Cherry | 55/194 X |
| 2,214,368 | 9/1940 | Greensfelder et al. | 55/195 X |
| 2,572,527 | 10/1951 | Sebald | 55/194 X |
| 2,668,598 | 2/1954 | Seed | 55/194 X |
| 2,816,500 | 12/1957 | Ehrman | 55/195 X |
| 2,882,995 | 4/1959 | Smith | 55/174 X |
| 3,135,113 | 6/1964 | Walker et al. | 55/168 X |
| 3,229,445 | 1/1966 | Kraft | 55/195 X |
| 3,347,023 | 10/1967 | Scott | 55/165 X |
| 4,089,662 | 5/1978 | Williams | 55/169 X |
| 4,392,874 | 7/1983 | Yamauchi | 55/194 |
| 4,684,345 | 8/1987 | Cattani | 55/164 X |

FOREIGN PATENT DOCUMENTS

| | | | |
|---|---|---|---|
| 647543 | 8/1962 | Canada | 55/164 |
| 8327965 | 11/1983 | Fed. Rep. of Germany | |
| 731202 | 4/1980 | U.S.S.R. | 55/194 |
| 239321 | 9/1925 | United Kingdom | 55/195 |

Primary Examiner—Robert Spitzer

[57] ABSTRACT

Apparatus for the degasification of flushing water from a water supply pipe, is provided in a degasification chamber with a measuring probe for stopping the water supply upon maximum filling and for switching-off of an adjustable continuous-flow heater which heats the flushing water and is associated with the water supply pipe, and with another measuring probe for freeing the water supply and for switching the heater on upon minimum filling, the water supply pipe being provided with a flow valve and opening by a spraying nozzle into the degasification chamber which is connected to a suction pump.

6 Claims, 1 Drawing Sheet

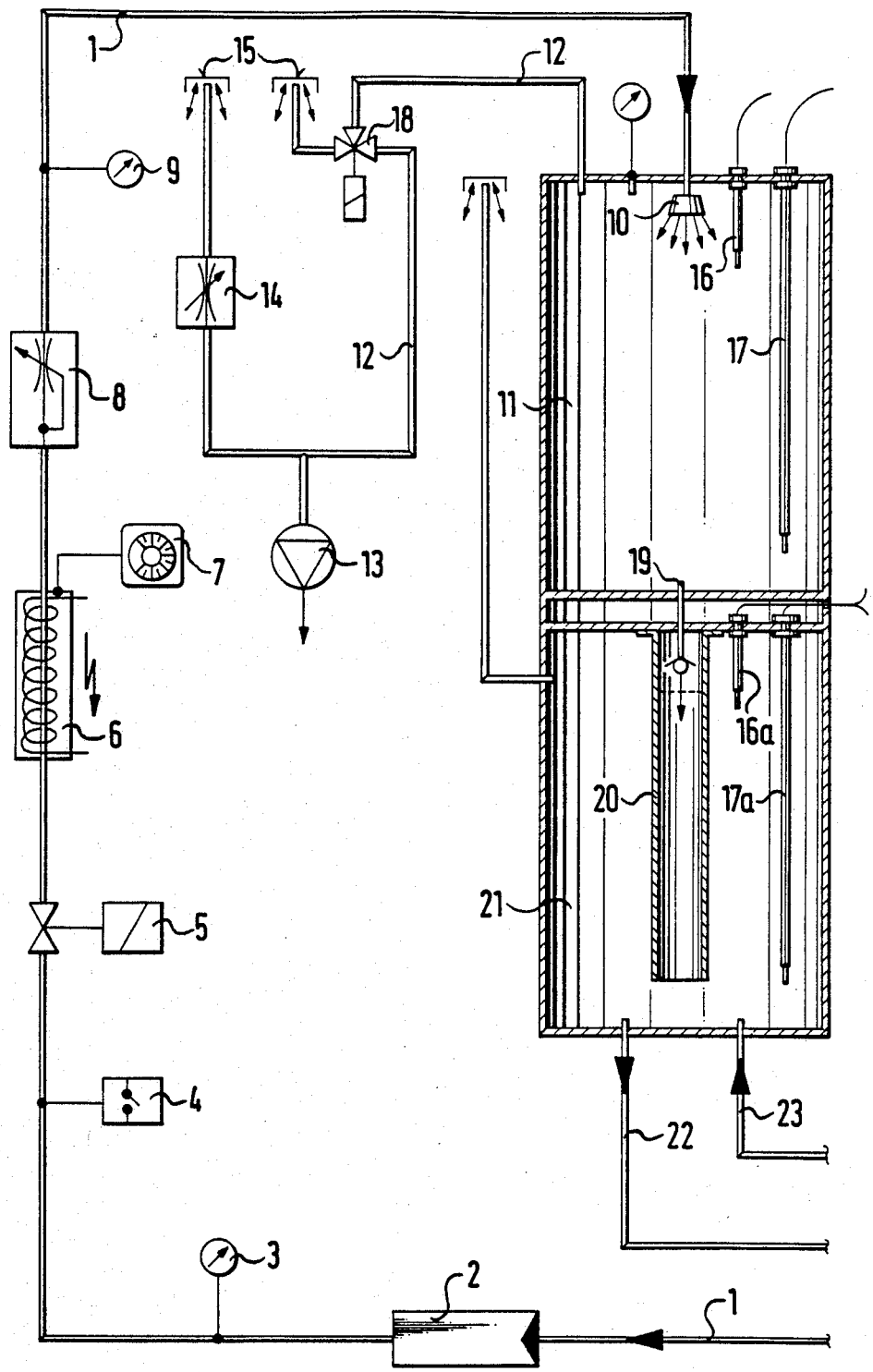

APPARATUS FOR THE DEGASIFICATION OF FLUSHING WATER

BACKGROUND OF THE INVENTION

1. Field of the Invention

The invention relates to an apparatus for the degasification of irrigating or flushing water which is to be introduced into body cavities and which is de-aerated or degasified in a first chamber, in which a measuring probe which is responsive to maximum filling stops the water supply and switches off a heater for heating the flushing water and a measuring probe which is responsive to minimum filling restarts the water supply and switches the heater on again. The water in the first chamber then flows into a second de-aeration or degasification charber, from which it is conducted into a filter plant for further treatment.

2. Description of the Prior Art

Such an apparatus is known from DE-GM 83 27 965 and operates by heating the flushing water in a first degasification or de-aeration chamber so that the gas bubbles resulting from the heating rise upwards and out of the water and can be removed. The degasified water then flows into a second de-aeration or degasification chamber from which it can then be conducted via a filter plant with an irrigator into a body cavity that is to be flushed. Although satisfactory degasification of the water is effected in most instances by such an apparatus, applicants have found that there are some specific instances in which the degasification is not sufficient e.g. when carrying out transurethral operations, using an endoscope, since the presence of residual gas bubbles in the flushing water impedes the view of the operator through the endoscope.

SUMMARY OF THE INVENTION

Therefore, the main object of the present invention is to provide a flushing liquid for the flushing of body cavities which does not have any disturbing gas bubbles which would impede the view of an operator using an endoscope.

To this end, the present invention consists of an apparatus for the degasification of flushing water which is to be introduced into a body cavity and which is degasified in a first chamber, said apparatus comprising an adjustable continuous-flow heater for heating the flushing water while passing through a water supply pipe, a measuring probe which is responsive to maximum filling to stop the water supply and to switch off the heater, another measuring probe which is responsive to minimum filling to restart the water supply and switch on the heater again, a second degasification chamber which receives the heated flushing water from the first degasification chamber and from which the heated flushing water passes into a filter plant, a flow regulating valve in the water supply pipe, a spray nozzle opening from the water supply pipe into the first degasification chamber and a suction pump connected through a feed pipe to the first degasification chamber to generate an underpressure or vacuum therein.

By means of the invention water from a drinking-water supply is heated in passage through the supply pipe to the first de-aeration chamber and is introduced through the spraying nozzle in the form of very small droplets of liquid into the first degasification chamber, so that it is, on the one hand, in this way and, on the other hand, as a result of the applied underpressure in the chamber by which the boiling point is reduced, degasified with extremely high efficiency.

In order, in this respect, to prevent the pump which generates the underpressure from working constantly in the saturation region, the pump is operated by way of an adjustable throttle valve with gas ballast, namely in such a way that a specific underpressure in the chamber is thereby not exceeded.

In order that the invention may be more readily understood an embodiment thereof will now be described, by way of example, with reference :o the accompanying drawing, which shows, diagrammatically an apparatus for the degasification of flushing water in body cavities.

BRIEF DESCRIPTION OF THE DRAWING

The FIGURE is a diagramatic illustration of an apparatus according to the present invention.

DESCRIPTION OF THE PREFERRED EMBODIMENT

Referring to the drawing, flushing water from a drinking-water pipe 1 is fed via a filter 2, along with measurement of the water pressure by a manometer 3 and a solenoid-operated shut-off valve 5 to a continuous-flow heater 6, with the pressure of the water in the pipe 1 just after of the filter 2 being measured by a manometer 3. The heater 6 has a regulating thermostat 7 for keeping the temperature of the water in pipe 1 constant. In this respect, there is, advantageously, provided in the pipe 1 a pressure switch 4 by which the further water supply is switched off as soon as maximum filling is reached, i.e. the filling is at its highest permissible value, or when the water pressure is too low.

The water heated in the heater 6 is fed through a regulating valve 8 which automatically limits the amount of water flowing therethrough and past a location where the water temperature is measured by a temperature measurement device 9 to a spray nozzle 10 which finely sprays the heated water into a first degasification or de-aeration chamber 11. The degasification chamber 11 is placed under a reduced pressure or vacuum by means of a suction pump 13 connected to the chamber 11 by a feed pipe 12. So that the pump 13 does not work constantly in the saturation region and so that the reduced pressure in the chamber 11 does not exceed a specific value, the pump 13 communicates with the atmosphere by way of an adjustable throttle valve 14 and by way of a ventilating or aeration valve 15, whereby secondary air is constantly sucked to maintain the reduced pressure in the chamber 11 at a constant value.

As a result of the finely distributed spraying of the heated water into the degasification chamber 11 and as a result of the reduced pressure in the chamber 11 by which the boiling point of the water is reduced, an extremely effective degasification of the water in the chamber 11 is achieved. Arranged in the degasification chamber 11 are two measuring probes 16 and 17 for the measurement of maximum and minimum filling respectively of the chamber. The probes 16 and 17 are both electrically connected by an electronic system (not shown) to the solenoid-operated shut-off valve 5 and the heater 6 to shut-off the water supply and switch off the heater when maximum filling is reached and upon minimum filling to open to valve 5 and switch on the heater 6, respectively.

The measuring probe 16 is, also, electrically, connected to an electronics system (not shown), which opens the solenoid-operated valve 18 in the feed pipe 12 from the pump 13 and connects the chamber 11 to the atmosphere as soon as the measuring probe 17a in a chamber 21 indicates a minimum filling, in which respect additionally the valve 5 is operated to shutoff the water supply and the heater 6 is switched off. By this means, the reduced pressure in the degasification chamber 11 is effectively cancelled so that for all practical purposes the chamber 11 is connected to the atmosphere or ambient air. Then degasified water runs out of the chamber 11 through a connecting pipe 19 which has a check or one way valve and which projects into a rising pipe 20 and into a second, lower, de-aeration or degasification chamber 21, from which the flushing water is conducted by way of a pipe 22 and a filter plant with an irrigator into the body cavity. Surplus flushing water runs back out of the filter plant by way of a reflux or return pipe 23 into the second chamber 21. The chamber 21 is likewise provided with two measuring probes 16a and 17a, responsive respectively to maximum and minimum filling of the chamber 21 to initiate operation of the solenoid valve 5 and switching of the heater 6 in the manner previously mentioned with regard to the chamber 11.

If, moreover, minimum filling of the chamber 11 is reached, then the solenoid valve 18 is again closed, the solenoid valve 5 opened and the continous-flow heater 6 switched on again, whereby the individual procedures are repeated.

Whilst a particular embodiment has been described, it should be appreciated that the invention includes all modifications, improvements and variations falling within its scope. For example, instead of the said measuring probes 16, 16a, 17, 17a, float switches or the like can be used for ascertaining the respective filling level.

What is claimed is:

1. Apparatus for the degasification of flushing water which is to be introduced into a body cavity and which is degasified in a first chamber, in which a measuring probe responsive to maximum filling stops the water supply and switches off a heater for heating the flushing water, another measuring probe responsive to minimum filling restarts the water supply and switches the heater on again and the heated water from the first degasification chamber flows into a second degasification chamber from which it is conducted into a filter plant, the improvement which comprises:

an adjustable continuous-flow heater which constitutes said heater for heating the flushing water and which is associated with a water supply pipe,
a flow regulating valve for said water supply pipe,
a spray nozzle by which said water supply pipe opens into the first degasification chamber,
and a suction pump communicating via a feed pipe with the first degasification chamber to generate an underpressure therein.

2. Apparatus according to claim 1, wherein the value of the underpressure in the first degasification chamber is adjustable to a maximum value, and, the suction pump is connected by an adjustable throttle valve and ventilating valve to the outside air.

3. Apparatus according to claim 1, wherein when the said maximum filling of the first degasification chamber is reached, the first mentioned measuring probe is operative to open a valve for the connection of the feed pipe to the outside air thereby to permit the flow of water out of the first degasification chamber and into the second degasification chamber from which such water is conductable into the filter plant.

4. Apparatus according to claim 1, characterised in that a connecting pipe having a rising pipe provided with a check valve is provided for the flow of the water out of the first degasification chamber into the second degasification chamber.

5. An apparatus for the degasification of flushing water which is to be introduced into a body cavity, said apparatus including a first chamber, a water supply line having a heater for heating water passing through the line, said water supply line terminating in a spray nozzle positioned in said first chamber, said first chamber having a first means for sensing a maximum filling level in said first chamber and stopping the water supply and switching off the heater when said maximum level is reached, said chamber having second means for sensing a minimum filling level and restarting the flow of water and switching on the heater when said minimum level is reached, a second chamber connected by valve means to said first chamber, and a suction pump connected by a feed pipe to said first chamber to create a vacuum in said first chamber.

6. An apparatus according to claim 5, wherein the valve means between the first and second chamber is a check valve blocking flow from the second to the first chamber, said feed pipe of the suction pump having means for venting the feed line to atmospheric pressure and said apparatus including means for actuating said means for venting to destroy the vacuum in the first chamber to enable fluid in the first chamber to pass through the check valve into the second chamber.

* * * * *